United States Patent [19]

Christian et al.

[11] Patent Number: 5,149,818

[45] Date of Patent: Sep. 22, 1992

[54] SYNTHESIS OF AMINONITROBENZODIFUROXAN

[75] Inventors: Stephen L. Christian; Andrew P. Chafin, both of Ridgecrest; Arnold T. Nielsen, Santa Barbara; Ronald L. Atkins, Ridgecrest; William P. Norris, Ridgecrest; Richard A. Hollins, Ridgecrest, all of Calif.

[73] Assignee: The United States of America as represented by the Secretary of the Navy, Washington, D.C.

[21] Appl. No.: 593,413

[22] Filed: Oct. 1, 1990

[51] Int. Cl.$^5$ .............................. C07D 271/12
[52] U.S. Cl. .................................... 548/126
[58] Field of Search ......................... 548/126

[56] References Cited

U.S. PATENT DOCUMENTS

| | | | |
|---|---|---|---|
| H476 | 6/1988 | Norris | 548/26 |
| 4,529,801 | 7/1985 | Norris | 548/126 |
| 4,754,040 | 6/1988 | Chafin | 548/126 |

FOREIGN PATENT DOCUMENTS 205898  1/1984  German Democratic Rep. ............................ 548/126

OTHER PUBLICATIONS

U.S. Statutory Invention Registration #H476, published Jun. 7, 1988, William P. Norris.

*Primary Examiner*—Robert Gerstl
*Attorney, Agent, or Firm*—Stuart H. Nissim; Melvin J. Sliwka; John L. Forrest, Jr.

[57] ABSTRACT

Aminonitrobenzodifuroxan (CL-18) is prepared by directly converting pentanitroaniline to aminonitrobenzodifuroxan with heat in the presence of an excess of sodium azide. The pentanitroaniline is prepared in high yield from 3,5-dinitroaniline with a mixture of nitric acid and sulfuric acid in which the final sulfuric acid concentration is from 99.0 to 99.5%.

10 Claims, 4 Drawing Sheets

SYNTHESIS OF AMINONITROBENZODIFUROXAN

TECHNICAL FIELD

The present invention relates to the synthesis of aminonitrobenzodifuroxan (CL-18) and, more particularly, this invention relates to the synthesis of CL-18 in high yield from commercially available starting material in a few steps.

BACKGROUND OF THE INVENTION

Insensitive explosive materials that are more energetic and denser than those currently employed are necessary to satisfy current and future military requirements. The nitrated benzofuroxans are a family of explosives that have these properties. Nitrated benzofuroxans and the salts of some of their derivatives have been investigated as potential military explosives.

Most nitrated benzofuroxans are quite dense (approaching 2.0 g/cc) since they consist of quaternary carbons, tertiary nitrogens, and a few or no hydrogens. Since the nitrated benzofuroxans contain both nitro groups and furoxan rings, they are energetic (D' = 7.9 to 9.0 mm/$\mu$s). In addition, most nitrated benzofuroxans have been found to be rather insensitive to impact, friction, and electrostatic shock relative to other explosives of similar energy. Benzotrifuroxan (BTF) is an important explosive. Other important explosives are 1,3,5-triamino-2,4,6-trinitrobenzene (TATB) and 1,3,5-trinitro-1,3,5-hexahydrotriazine (RDX). Another benzofuroxan, aminonitrobenzodifuroxan (CL-18) has a higher melting point than its trinitro analogues but not as high as the dinitro compound, 7-amino-4,6-dinitrobenzofuroxan (ADNBF). The measured density and detonation velocity compares favorably to that of the other benzofuroxans and its impact sensitivity is favorable.

Aminonitrobenzodifuroxan (4-amino-5-nitrobenzo [1,2-c:3, 4-c'] bis [1,2,5] oxadiazole-3,8-dioxide) has been previously prepared in 24% overall yield from 1,3,5 trifluorobenzene as shown in FIG. 1: 1,3,5-trifluorobenzene was added to a solution of potassium nitrate and fuming sulfuric acid. The mixture was heated to produce 1,3,5-trifluoro-2,4,6-trinitrobenzene (3) (Reference 1). The trifluoro compound 3 was treated with acetamide in refluxing benzene to give 1 acetamido-3,5-difluoro-2,4,6-trinitrobenzene (4) (Reference 2). A solution of 4 in concentrated sulfuric acid poured onto crushed ice produced 1-amino-3,5-difluorotrinitrobenzene (5). The amine 5 was treated with sodium azide in acetonitrile-water to give the diazide 6, which when dissolved in toluene and heated at reflux produces aminonitrobenzodifuroxan (1, CL-18).

CL-18 was also prepared by employing the formamide and urea derivatives (5 and 6 where NH$_2$ = NHCHO and NHCONH$_2$, respectively) to form derivatives of 1 with these substituents. These derivatives were also subsequently hydrolyzed to 1.

The trifluorobenzene is an expensive starting material and the synthesis based on this starting material requires 5 steps and the isolation of four different intermediates.

This synthesis is economically inefficient and does not reliably produce high purity CL-18. This method often results in the production of mixtures of CL-18 with other benzofuroxan derivatives or in the production of low-purity CL-18. It is not recommended for scale up to a pilot plant or commercial plant for production of large quantities of CL-18.

STATEMENT OF THE INVENTION

A new and improved synthesis of aminonitrobenzodifuroxan is provided by the present invention. The synthesis of the invention has fewer steps and prepares aminonitrobenzodifuroxan in high yield from a commercially available starting material. The synthesis of the invention does not require isolation of as many intermediates and aminonitrobenzodifuroxan is produced in pure form, not mixed with other reaction products or by products and needs no further processing for use as an explosive. However, since aminonitrobenzodifuroxan is soluble in a variety of solvents it can be readily recrystallized to increase purity or to control particle size.

The synthesis of the invention provides aminonitrobenzodifuroxan in high yield and at low cost. It is reproducible and is capable of being scaled to pilot plant or to production plant volumes.

In the synthesis of the invention, pentanitroaniline is directly converted to aminonitrobenzodifuroxan with heat in the presence of an excess of sodium azide. Though 3,5-diazido-2,4,6-trinitroaniline forms as an intermediate, it is dissolved in the reaction solvent and is not isolated. Ring closure to the benzodifuroxan proceeds and aminonitrobenzodifuroxan precipitates from the solution.

Pentanitroaniline (PNA) can be prepared by several different routes. It can be prepared by nitration of 4-amino-2,6-dinitroaniline (a reduction product of TNT) as disclosed in U.S. Pat. No. 4,248,798, the disclosure of which is expressly incorporated herein by reference. However, it has been discovered in accordance with the invention that PNA can easily be prepared in high yield from benzoic acid or dinitrobenzoic acid which are first converted to 3,5-dinitroaniline.

The invention also relates to the optimization of the conversion of 3,5-dinitroaniline to PNA. It was discovered that the sulfuric acid concentration must be controlled within a narrow range of 99.0 to 99.5 percent by weight in order to maximize the yield of PNA.

These and many other features and attendant advantages of the invention will become apparent as the invention becomes better understood by reference to the following detailed description when considered in conjunction with the accompanying drawings.

DETAILED DESCRIPTION OF THE INVENTION

The conversion of pentanitroaniline to aminonitrobenzodifuroxan can be conducted in totally organic media or in the presence of water. In the organic phase synthesis, PNA is converted to CL-18 in 2 steps. When PNA is dissolved in an organic solvent such as acetic acid at room temperature and allowed to react with a slight excess of four equivalents of an alkali metal azide, 3,5-diazido-2,4,6-trinitroaniline is generated. After about 10 minutes of stirring, ring closure occurs and CL-18 starts precipitating. Heating the reaction mixture to a temperature above room temperature, typically from 50° C. to 120° C. accelerates the conversion. After the reaction is complete, the reaction mixture is cooled to room temperature and the pure, crystalline CL-18 is recovered by filtration and is washed with water and dried.

In an alternate procedure, pure PNA is dissolved in a solvent such as dichloroethane at room temperature and is reacted with slightly more than 2 equivalents (usually a 3-10% excess) of sodium azide dissolved in water. The diazide compound is generated as in the first procedure. The dichloroethane layer containing the diazide is separated from the water layer and dried over desiccant such as magnesium sulfate. The dried solution is heated at reflux for about ½ an hour. On cooling to room temperature the CL-18 precipitates. The precipitate can be separated by filtration and is then washed with solvent and dried.

The disadvantage of the second procedure is that a larger volume of solvent is required to dissolve the PNA. An advantage of the second procedure is that a lower amount of sodium azide is required. In the first procedure, a much smaller volume of acetic acid solvent is utilized. Also the CL-18 which crystallizes from the acetic acid is purer than the CL-18 crystallizing from dichloroethane as determined by melting point and infrared analysis. In addition the yield of CL-18 from the first procedure is higher (73% versus 58%). For these reasons the single phase synthesis is the preferred route.

Figure 2:
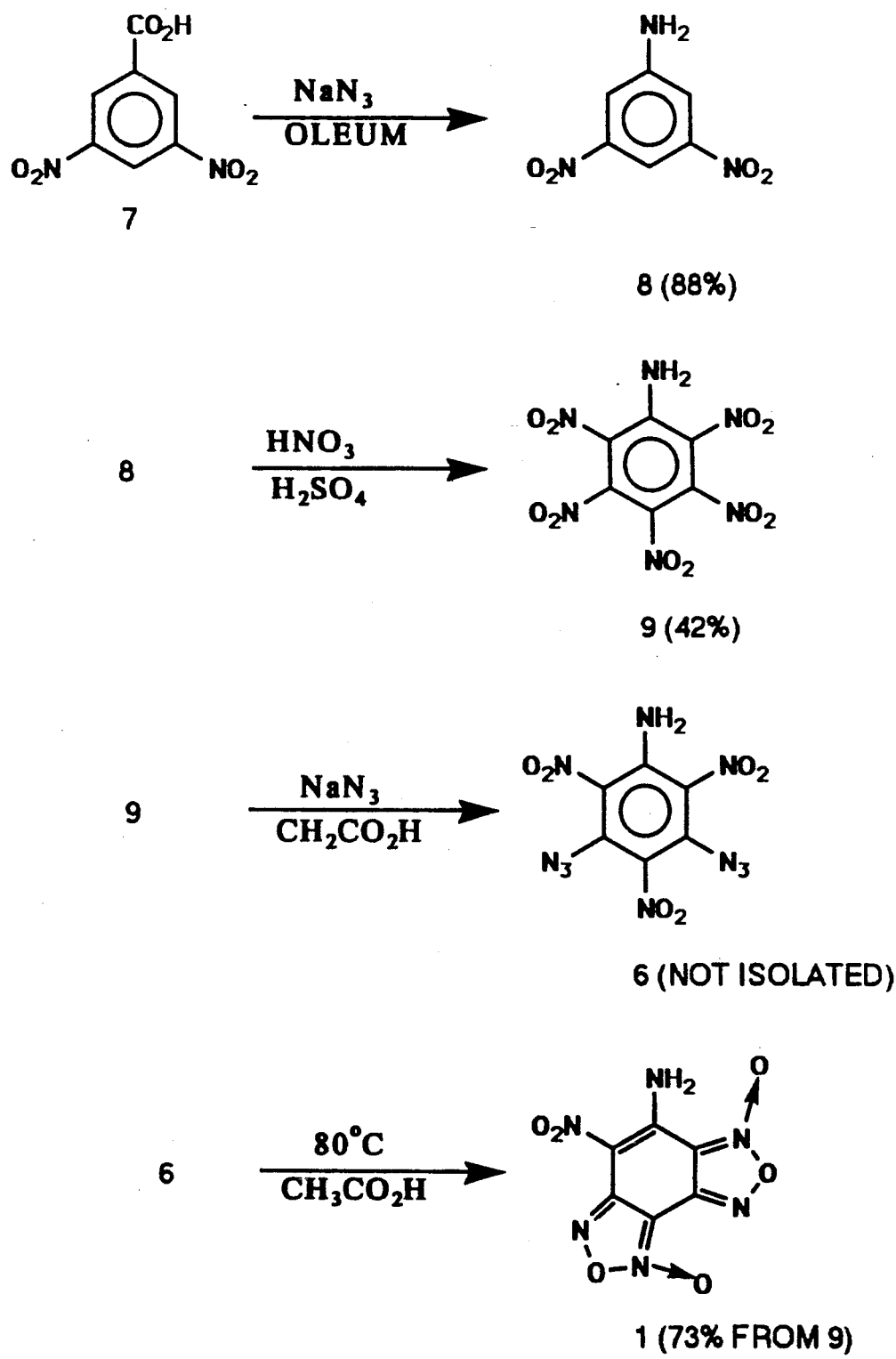
FIG. 2 is a reaction sequence of the first synthesis of aminonitrobenzodifuroxan from dinitrobenzoic acid.

Referring now to FIG. 2 commercially available 3,5-dinitrobenzoic acid (7) was converted to 3,5-dinitroaniline (8) through a Schmidt reaction. Several preparations run in a 3-liter flask (about 1 liter of reactants) routinely produced the amine 8 in 86 to 88% yield. The crude material was sufficiently pure to use for further reactions. 3,5-dinitrobenzoic acid (7) is made by nitration of benzoic acid in 60% yield (Reference 3). 3,5-dinitroaniline may also be prepared by reduction of 1,3,5-trinitrobenzene with ammonium sulfide (Reference 4).

3,5-dinitroaniline (8) was converted into pentanitroaniline (9) by nitrating with a mixture of 90% nitric acid and sulfuric acid. A slight excess of 10 equivalents of nitric acid is sufficient to achieve full nitration of the aromatic ring. The conversion of 8 to 9 is the critical step in the synthesis of CL-18 by this route. Much effort was expended to optimize the preparation of 9. After careful study, a final sulfuric acid concentration of 99.0 to 99.5%, a reaction time of 1½ hours at 70° C., followed by cooling to room temperature, and extraction of the acid mixture with dichloroethane were required to produce the best yield (about 42%) and highest purity of 9. Using a sulfuric acid concentration lower than 99% resulted in low yields of 9, and in many cases, diazooxide formation occurred along with fumeoffs (runaway thermal reactions). A final sulfuric acid concentration greater than 99.5% also gave low yields of 9. The overall yield of 9 from 3,5-dinitrobenzoic acid (2 steps) is 37% and from benzoic acid is 22% (3 steps).

Pure 9 can be converted to CL-18 by two procedures. In Procedure A, pure 9 is dissolved in acetic acid at room temperature and allowed to react with a slight excess of four equivalents of sodium azide. Nitrous and hydrazoic acids which are produced react to form nitrosyl azide (Reference 5). Since two moles of $HNO_2$ are formed by azide displacement, two additional moles of azide are required; a total of four moles of azide is needed to complete the reaction. Reaction of 9 with azide ion generates 3,5-diazido-2,4,6-trinitroaniline (6) (not isolated) in solution, and after approximately 10 minutes of stirring, ring closure occurs, and CL-18 begins to precipitate out of the solution. The mixture is heated to 80° C. to complete the reaction. After cooling and standing at room temperature overnight, the pure crystalline CL-18 is filtered, washed with water, and air dried.

Figure 3:
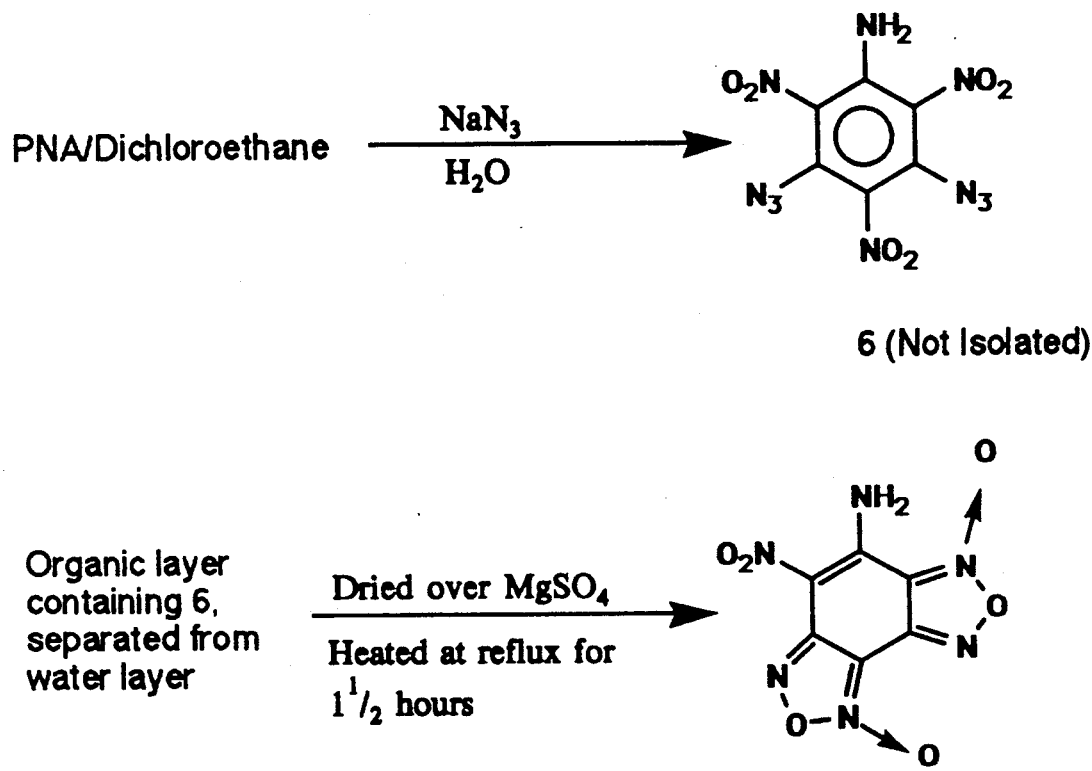
FIG. 3 is a reaction sequence showing an alternative conversion of PNA to aminonitrobenzodifuroxan.

In Procedure B, shown in FIG. 3, pure 9 is dissolved in dichloroethane at room temperature and treated with slightly more than two equivalents of sodium azide dissolved in water. The diazido compound 6 is generated in solution as in Procedure A but is not immediately converted into CL-18. The dichloroethane solution is separated from the water layer, dried over magnesium sulfate, and heated at reflux for 1½ hours. On cooling to room temperature, the CL-18 precipitates and can be filtered off, washed with dichloroethane, and air dried. The diazido 6 is not isolated in either Procedure A or B because of its potential shock sensitivity. Also, since 6 can be reacted while in solution to produce the desired CL-18, its isolation is unnecessary.

Figure 4:
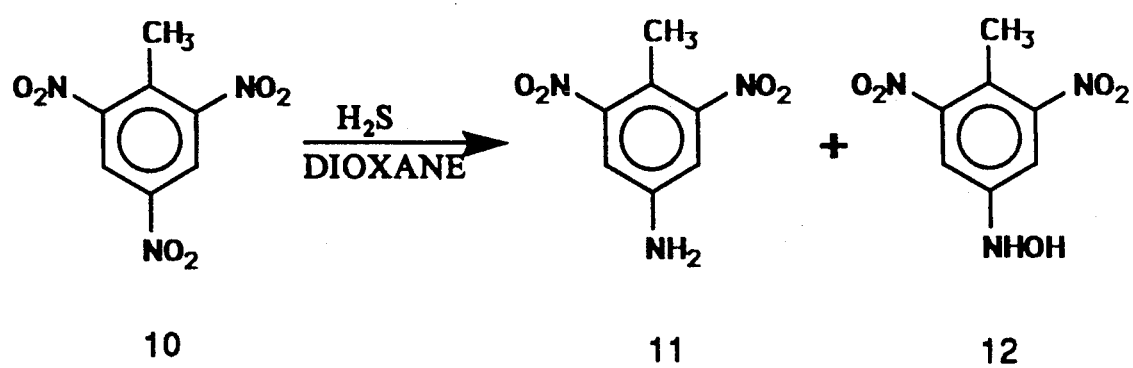
FIG. 4 is a reaction sequence showing the preparation of PNA from 2,4,6-trinitrotoluene.
Figure 4:
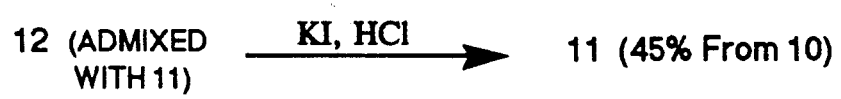
Figure 4:
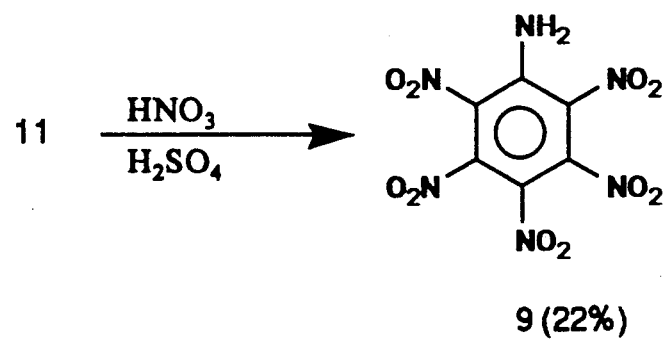

An alternate method of pentanitroaniline synthesis, based on a recent patent (Reference 6), was examined (FIG. 4). 2,4,6-trinitrotoluene (TNT) (10) is dissolved in p-dioxane and $H_2S$ gas is bubbled through the solution holding the temperature below 50° C. The sulfur which precipitates is filtered off and the filtrate is poured over ice mixed with water to produce a mixture of the desired intermediate 4-amino-2,6-dinitrotoluene (11) and the partially reduced product 2,6-dinitro-4-hydroxylaminotoluene (12); the ratio of 11:12 usually is 3:2, but varies from 1:2 to 2:1. The crude mixture of 11 and 12 is suspended in hydrochloric acid and treated with potassium iodide. The hydrochloric acid and potassium iodide form hydroiodic acid (HI) which serves as the reducing agent to convert the hydroxylamine 12 into the amine 11. Cooling, filtration, and recrystallization provide the desired 11 in 45% overall yield from TNT. The amine 11 is nitrated using concentrated sulfuric acid/90% nitric acid with heating to 80° C. (Under these nitration conditions, the methyl group on the amine is oxidized, carbon dioxide is liberated, and subsequent nitration occurs at this position on the aromatic ring.) The nitrated mixture is allowed to cool to 60° C. and then extracted with dichloroethane. The extract is dried and concentrated to produce pentanitroaniline (9) in 22% yield (10% overall yield from TNT).

Figure 1:
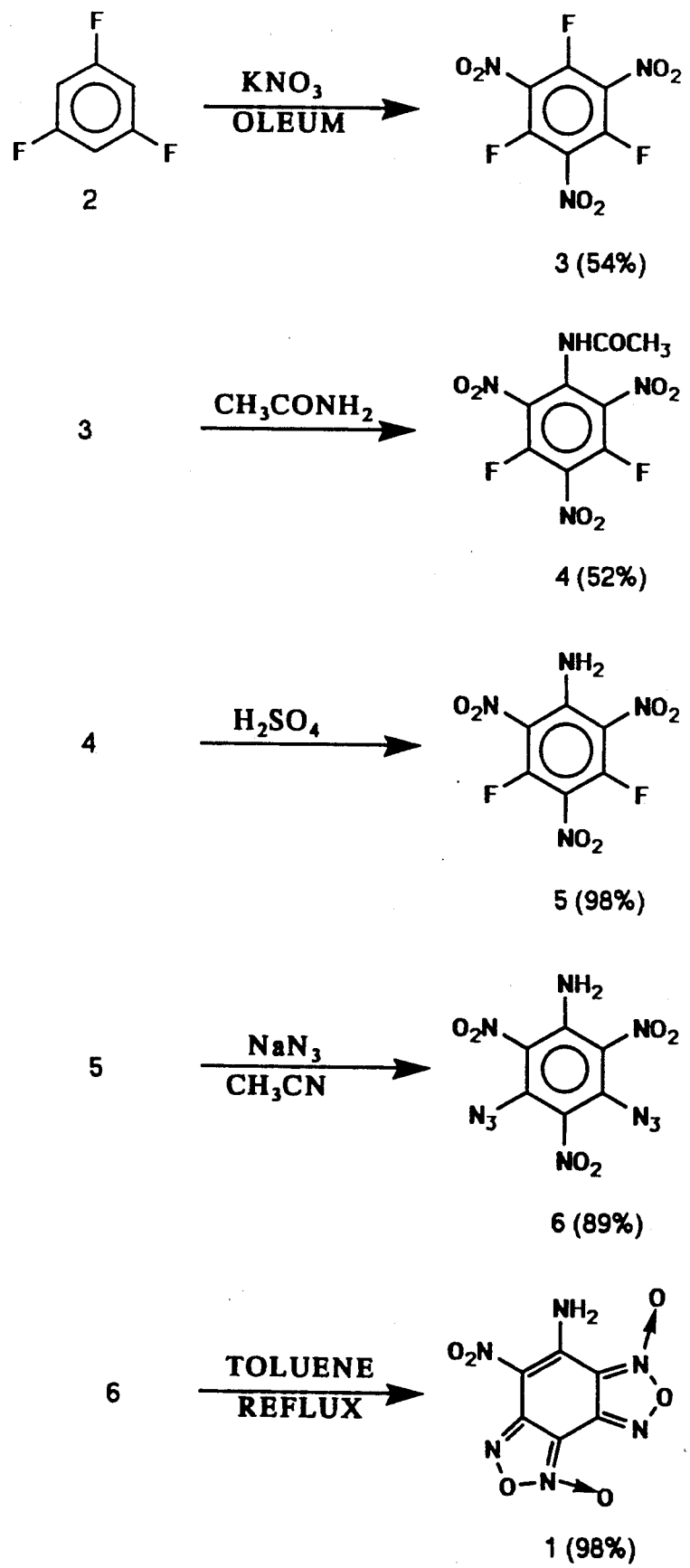
FIG. 1 is a reaction sequence of the prior art synthesis of aminonitrobenzodifuroxan from 1,3,5-trifluorobenzene.

The overall yield of CL-18 obtained using 3,5-dinitrobenzoic acid as the starting material is 27% (FIG. 2); starting from benzoic acid, the overall yield is 16%. The prior art procedure (FIG. 1) provides a 24% overall yield starting from 1,3,5-trifluorobenzene. The synthesis of FIG. 1 requires five steps and isolation of four intermediates to prepare CL-18, whereas the method of the invention requires only four steps and isolation of only two intermediates. The starting material for the prior art synthesis (1,3,5-trifluoroenzene) is quite expensive compared with the starting material for FIG. 2 (3,5-dinitrobenzoic acid). FIG. 2 is believed to be the best method for synthesizing CL-18 (least number of steps and highest overall yield from a relatively inexpensive starting material). Using the method of the invention CL-18 should be scaleable to pound quantities for further testing.

PHYSICAL PROPERTIES OF CL-18

Some important properties of CL-18 are compared with those of other benzofuroxan explosives, 1,3,5-triamino-2,4,6-trinitrobenzene (TATB) and 1,3,5-trinitro-1,3,5-hexahydrotriazine (RDX) in Table 1. Aminonitrobenzodifuroxan has a higher melting point than its trinitro analogues but not as high as the dinitro compound, 7-amino-4,6-dinitrobenzofuroxan (ADNBF); the measured density compares favorably with the densities of the other benzofuroxans as well as TATB; the calculated detonation velocity lies between that of the trinitro and dinitro analogues; the detonation velocity is noticeably higher than that of TATB; the impact sensitivity is similar to that of TNT. The melting point of CL-18 is the same as RDX, but the density of CL-18 is greater and its sensitivity is less; the energies are comparable.

TABLE 1

Properties of CL-18 and Other Benzofuroxan Explosives, TATB and RDX

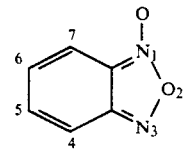

| Benzofuroxan substitution | Melting point, °C. | Density g/cm$^3$ | Detonation velocity, mm/μs | Impact sensitivity, H$_{50}$, cm$^a$ |
|---|---|---|---|---|
| 7-NH$_2$-6-NO$_2$-4,5-difuroxano- (CL-18) | 205 | 1.93$^b$ | (8.37)$^c$ | 56 |
| 7-NH$_2$-4,6-(NO$_2$)$_2$ (ADNBF) | 270 | 1.90 | 7.91 | 53 |
| 4,5,6-(NO$_2$)$_3$— | 115 | (1.95)$^c$ | (8.43)$^c$ | — |
| 7-NH$_2$-4,5,6-(NO$_2$)$_3$—(CL-17) | 175 | 1.87 | (8.57)$^c$ | 56 |
| TATB | 350 | 1.94 | 7.94 | 300 |
| RDX | 204 | 1.82 | 8.75 | 25 |

$^a$2.5 kilograms weight: TNT = 54 centimeters; values determined on the impact tester of NWC's Research Department.
$^b$Determined by X-ray analysis (Reference 7).
$^c$Calculated values in parenthesis (References 8 and 9).

Impact, friction, and electrostatic test results on CL-18 are compared with those for the commonly used explosives RDX and Composition B (60% RDX/40% TNT) in Table 2.

The test results indicate that CL-18 is less susceptible to initiation by impact and friction than 1,3,5,8-tetranitro-1,3,5,8-tetraazacyclooctane (HMX), RDX, and Composition B. However, CL-18 appears to be more susceptible to electrostatic initiation.

TABLE 2

Sensitivity Properties of CL-18, RDX, and Composition B

| Compound | Impact, H$_{50}$, cm$^a$ | Friction | Electrostatic at 0.25 J |
|---|---|---|---|
| CL-18 | 33 | 10/10 NF at 794 lbs | 14/20 NF |
| RDX | 15 | 10/10 NF at 316 lbs | 10/10 NF |
| Composition B | 19 | 10/10 NF at 316 lbs | 10/10 NF |

$^a$Values determined on the impact tester of NWC's Ordnance Systems Department.

CONCLUSIONS

Sensitivity and performance evaluation on CL-18, thus far, suggest that this explosive has properties superior to certain currently used military explosives. In addition, CL-18 is readily soluble in a variety of solvents which would facilitate recrystallization and allow its particle size to be controlled. This should allow facile formulation of CL-18-based explosives.

EXPERIMENTAL SECTION

Infrared (IR) spectra were determined on a Perkin-Elmer Model 137 or a Perkin-Elmer Model 1330 infrared spectrophotometer. Mass spectra were determined on a Hewlett-Packard Model 5985 gas chromatograph/mass spectrometer (GC/MS). Nuclear magnetic resonance (NMR) spectra were determined on an IBM NR80 spectrometer using tetramethylsilane as an internal reference. Melting points were determined on a Kofler hot stage apparatus and are uncorrected. Elemental analyses were performed by Galbraith Laboratories, Knoxville, Tennessee.

Preparation of 3,5-Dinitroaniline (8)

3,5-Dinitrobenzoic acid (7, Aldrich) (106.1 grams, 0.50 mole) was dissolved in 400 milliliters of 23 to 24% oleum. Dichloroethane (480 milliliters) was added to this solution. Sodium azide (37 grams, 0.57 mole) was added in portions with stirring while maintaining the temperature below 25° C. The mixture was heated under reflux for 4 hours and allowed to cool to room temperature. The dichloroethane was removed by decantation, and the remaining mixture was poured over 9 liters of ice mixed with water. The yellow solid which separated was filtered, washed with water, and air dried to afford 80.5 grams (87.9%) of 8 with a melting point of 158° to 162° C.; literature: melting point of 162° to 163° C. (Reference 10). IR (KBr) 3335, (d, NH$_2$), 3035, 1615 (C=O), 1575, 1525, 1440, 1325, 1090, 1050, 990, 915, 880, 810 and 730 cm$^{-1}$.

Preparation of Pentanitroaniline (9)

3,5-Dinitroaniline (8 good purity), 18.3 grams, 0.10 mole) was added to a mechanically stirred solution of 550 milliliters of 100.0% H$_2$SO$_4$ (assayed carefully by NaOH titration) and 5.28 grams of ice, which had been stirred sufficiently beforehand to form 99.5% H$_2$SO$_4$. During addition the temperature was maintained below 35° C. When the dinitroaniline had all dissolved, 50.0 milliliters (1.07 moles) of pure 90% HNO$_3$ in 100 milliliters of 100.0% H$_2$SO$_4$ was added dropwise keeping the temperature below 30° C. (The final total mixed acid concentration at this point is 99.0%.) The mixture was heated to 70° C. during 1¼ hours (hot water bath) and stirred at this temperature for 1½ hours. The solution was cooled to 25° C. without stirring and without removing the reaction flask from the cooling water bath. The mixture was extracted with three 1-liter portions of dichloroethane; the extracts were combined and stirred with MgSO$_4$ overnight. The mixture was filtered and the filtrate was concentrated to approximately 400 milliliters on the rotoevaporator. The mixture was stored at −15 ° C. overnight, filtered on a medium sintered-glass funnel, washed once with 5 milliliters of cold dichloroethane, and air dried to afford 13.46 grams (42.3%) of pure crystalline pentanitroaniline (9), melting point 200° to 208° C. IR (KBr) 3335, (d, NH$_2$), 1640, 1610, 1590, 1560, 1540, 1460, 1425, 1360, 1325, 1290, 1170, 920, 895, 835, 805, and 790 authentic sample, melting point 210° to 211° C. (Reference 11).

In a parallel run, the combined dichloroethane extracts were concentrated to dryness to afford a 56% yield of crude pentanitroaniline (melting point 130° to 194° C.). The 42.3% yield of pure pentanitroaniline represents a 75% recovery from the crude mixture. The data suggest that only a small amount of impurities are present in the crude pentanitroaniline mixture and it may be possible to use it for direct conversion into CL-18 (1).

In an alternate work up procedure which avoids extraction with a solvent, the crude pentanitroaniline 9 was allowed to precipitate from the cool acid reaction mixture, removed by filtration, and washed with concentrated $H_2SO_4$, 50% $H_2SO_4$, and 1 Normal of HCl (30 to 43% yield, melting point 148° to 185° C.). Recrystallization of this material from various solvents gave poor recovery of pure 9.

Preparation of Aminonitrobenzodifuroxan (CL-18, 1)

Procedure A

Pure pentanitroaniline (9, 2.0 grams, 6.3 millimoles) was dissolved in 20 milliliters of acetic acid at 25° C. Sodium azide (1.63 grams, 25.1 millimoles) was added in portions to the solution while keeping the temperature below 32° C. The solution was stirred at 25° C. for 15 minutes, then heated (hot water bath), and allowed to stir at 80° C. for 1 hour. The solution was allowed to cool to 25° C. overnight. The yellow precipitate was filtered on a medium sintered-glass funnel, washed twice with 25 milliliters of water, and air dried to afford 1.17 grams (73.1%) of CL-18 (1), melting point 205° to 210° C.; recrystallization from boiling acetic acid gave rectangular prisms, melting point 201° to 204° C., with previous phase change at 186° to 195° C. (75% recovery). Analysis calculated for $C_6H_2N_6O_6$: C, 28.36; H, 0.79; N, 33.07. Found: C, 28.44; H, 0.79; N, 33.03.

Procedure B

Pure pentanitroaniline (9, 5.0 grams, 15.7 millimoles) was dissolved in 800 milliliters of dichloroethane at 25° C. by mechanical stirring. Sodium azide (2.14 grams, 32.9 millimoles) in 50 milliliters of water was added to the solution dropwise while keeping the temperature below 30° C. The mixture was stirred for 1 hour at 25° C. The dichloroethane layer was separated from the water layer and dried over $MgSO_4$ for 2 hours. The $MgSO_4$ was filtered off; the filtrate was refluxed for 1½ hours and allowed to cool to 25° C. The yellow precipitate was filtered off, washed once with 50 milliliters of dichloroethane, and air dried to yield 2.32 grams (58.1%) of CL-18 (1), melting point 185° to 200° C.; IR (KBr) 3320 (d, $NH_2$), 1655, 1625, 1570, 1490, 1450, 1430, 1390, 1360, 1320, 1285, 1250, 1110, 1075, 1010, 970, 930, 855, 805, 770, 755, 685, 660, 625 and 465 $cm^{-1}$.

Analysis calculated for $C_6H_2N_6O_6$: C, 28.36; H, 0.79; N, 33.07. Found: C, 28.13; H, 0.76; N, 33.08.

List of Cited References

1. U.S. Pat. No. 4,173,591 Koppes et al.
2. William M. Koppes, G. William Lawrence, Michael E. Sitzmann, and Horst G. Adolph. "Reaction of 1,3,5-Trifluorotrinitrobenzene With Nucleophiles", J.C.S Perkin I, 1981, pp. 1815-20.
3. Ross Phillips, "Organic Synthesis", Collective Vol. III, E.C. Horning ed., New York, Wiley, 1955, pp. 337-38.
4. Ben H. Nicolet. "Positive Halogens Attached to Carbon in the Aromatic Series V. Analogy Between Positive and Negative Halogens", J. Am. Chem. Soc., Vol. 49 (1927), pp. 1810-14.
5. G. Stedman. "Mechanism of the Azide-Nitrite Reaction, Part IV", J. Chem. Soc., 1960, pp. 1702-09.
6. U.S. Pat. No. 4,248,798 Atkins et al.
7. Herman L. Ammon and Sovan K. Bhattacharjee. "Crystallographic Studies of High-Density Organic Compounds: 4-Amino-5-nitrobenzo[1,2-c:3,4-c']bis[1,2,5]oxadiazole-3,8-Dioxide", Acta Cryst., B38 (1982), pp. 2498-2502.
8. Dorothy A. Cichra, James R. Holden, and Charles R. Dickinson. "Estimation of Normal Densities of Explosives from Empirical Atomic Volumes", Naval Surface Weapons Center publication, UNCLASSIFIED, NSWC-TR-79-273, February 1980.
9. L. R. Rothstein and R. Petersen. "Predicting High Explosive Detonation Velocities From Their Composition and Structure", Prop. and Explo., Vol. 4 (1979), pp. 56-60; Vol. 6 (1981), pp. 91-3.
10. W.C. Lothrop, G.R. Handrick, and R.M. Hainer, "The Structure and Infrared Absorption Spectra of Polynitrophenylmethylnitramines and Polynitroanilines," J. Am. Chem. Soc., 73 (1951), pp. 3581-84.
11. Arnold T. Nielsen, Ronald L. Atkins, William P. Norris, Clifford L. Coon, and Michael E. Sitzman, "Synthesis of Polynitro Compounds. Peroxydisulfuric Acid Oxidation of Polynitroarylamines to Polynitro Aromatics," J. Org. Chem., 45 (1980), pp. 2341-47.

It is to be realized that only preferred embodiments of the invention have been described and that numerous substitutions, modifications and alterations are permissible without departing from the spirit and scope of the invention as defined in the following claims.

What we claim is:

1. A method of synthesizing aminonitrobenzodifuroxan, comprising the steps of:
    (a) dissolving pentanitroaniline in a solvent;
    (b) adding an alkali metal azide to the pentanitroaniline solution;
    (c) stirring the solution; and,
    (d) recovering the aminonitrobenzodifuroxan.

2. The method of claim 1, wherein the solvent is an organic solvent.

3. The method of claim 1 wherein the solvent is acetic acid.

4. The method of claim 1 wherein, the amount of alkali metal azide added is about four equivalents.

5. The method of claim 1 wherein, the alkali metal azide is sodium azide.

6. The method of claim 1 wherein, the product is recovered by filtration.

7. The method of claim 1 wherein, after step c) the reaction heated to about 50° C. to 120° C.; stirred; and allowed to cool before step d), recovering the product.

8. The method of claim 2 wherein, in step b) the alkali metal azide is dissolved in water, and then the alkali metal oxide solution is added to the pentanitroaniline solution; and,
wherein, step d) is comprised of the following steps:
    i) separating the organic layer;
    ii) drying the organic layer;
    iii) refluxing the organic layer;
    iv) cooling the refluxed organic layer; and,
    v) recovering the product by filtration.

9. The method of claim 8 wherein, the amount of alkali metal azide dissolved is about two equivalents.

10. The method of claim 8 wherein, the solvent is dichloroethane, and, wherein the alkali metal azide is sodium azide.

* * * * *